(12) United States Patent
Valavi

(10) Patent No.: US 8,571,598 B2
(45) Date of Patent: Oct. 29, 2013

(54) METHOD AND APPARATUS FOR LOCATION-BASED WIRELESS CONNECTION AND PAIRING

(75) Inventor: John J. Valavi, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 882 days.

(21) Appl. No.: 11/640,489

(22) Filed: Dec. 18, 2006

(65) Prior Publication Data

US 2008/0146265 A1  Jun. 19, 2008

(51) Int. Cl.
*H04M 1/00* (2006.01)
*H04W 24/00* (2009.01)

(52) U.S. Cl.
USPC .................. 455/550.1; 455/456.6

(58) Field of Classification Search
USPC ............. 455/404.2, 412.1, 419, 404.1, 556.1, 455/466; 370/338, 310, 335
See application file for complete search history.

(56) References Cited

U.S. PATENT DOCUMENTS

| | | | |
|---|---|---|---|
| 7,386,517 B1 * | 6/2008 | Donner | 705/75 |
| 7,415,424 B1 * | 8/2008 | Donner | 705/10 |
| 2003/0110291 A1 * | 6/2003 | Chen | 709/244 |
| 2005/0153729 A1 * | 7/2005 | Logan et al. | 455/550.1 |
| 2006/0010203 A1 * | 1/2006 | Mrsic-Flogel et al. | 709/205 |
| 2006/0205354 A1 * | 9/2006 | Pirzada et al. | 455/66.1 |
| 2006/0294247 A1 * | 12/2006 | Hinckley et al. | 709/228 |
| 2007/0123166 A1 * | 5/2007 | Sheynman et al. | 455/41.2 |
| 2007/0132733 A1 * | 6/2007 | Ram | 345/163 |
| 2007/0176745 A1 * | 8/2007 | Gibson et al. | 340/10.1 |
| 2007/0282208 A1 * | 12/2007 | Jacobs et al. | 600/485 |
| 2008/0021777 A1 * | 1/2008 | Mack et al. | 705/14 |
| 2008/0080455 A1 * | 4/2008 | Rofougaran | 370/342 |
| 2008/0081667 A1 * | 4/2008 | Parikh et al. | 455/558 |
| 2008/0092043 A1 * | 4/2008 | Trethewey | 715/705 |
| 2008/0120311 A1 * | 5/2008 | Reed et al. | 707/100 |
| 2008/0176516 A1 * | 7/2008 | Kim | 455/41.2 |
| 2008/0232605 A1 * | 9/2008 | Bagha | 381/67 |
| 2008/0261564 A1 * | 10/2008 | Logan | 455/413 |

* cited by examiner

*Primary Examiner* — Michael Faragalla
(74) *Attorney, Agent, or Firm* — Pillsbury Winthrop Shaw Pittman LLP

(57) ABSTRACT

A method for wireless communication between a first device and a peripheral device comprises providing a storage device adapted to store communication information for the peripheral device and being readable by the first device, the storage device being spatially separated from the peripheral device. The method also comprises positioning the device so that the first device can read communication information for the peripheral device before communicating with the peripheral device. An apparatus comprises a storage device including data for wireless communication between a first device and a peripheral device within a location, the apparatus being positioned in or near the location and adapted for storing communication information for the peripheral device. The communication information can be read by the first device, allowing the first device to communicate with the peripheral device.

36 Claims, 15 Drawing Sheets

Process 1                           Process 2

METHOD AND APPARATUS FOR LOCATION-BASED WIRELESS CONNECTION AND PAIRING

FIELD OF INVENTION

The embodiments of the invention relate to location-based wireless communication connection and pairing for computers and peripherals. The embodiments of the present invention relate more specifically to using a device for storing location-specific connection and pairing information, for use in location-based wireless communication between computers and peripherals.

BACKGROUND

Known computers, including mobile computers, benefit from the use of wireless communication protocols, particularly with respect to peripheral devices that are used with the computer. Using a standardized wireless technology, such as Bluetooth, allows standardized communication between a computer and integrated wireless peripherals. Bluetooth is an industrial specification for wireless personal area networks (PANs) and utilizes the 2.4 GHz ISM band. Bluetooth is based on a short-range radio link, so that line-of-sight connection is not always required. Bluetooth provides a way to connect and exchange information between devices such as personal digital assistants (PDAs), mobile phones, laptops, PCs, printers, digital cameras, and video game consoles via a secure, globally unlicensed, short-range radio frequency.

Wireless communication, for example between a computer and a peripheral via a wireless communication protocol such as Bluetooth, can require that connection and pairing take place, which can be time consuming when there are numerous devices with which to pair. Thus, as used herein, wireless communication can include both connection and pairing. For security reasons, two Bluetooth-enabled devices may need to be paired before they can exchange data. The term "pairing" refers to the two devices exchanging a protected security identification number, or passkey. The term "connection" refers generally to two devices exchanging appropriate information to begin communication. In the context of Bluetooth wireless communication, connection can more specifically refer to the process of performing an inquiry to find another device or trying to connect to a known address for another device, and receiving a response from the other device that may include its name, class, and a list of services. Use of a device's services, following connection, may require pairing, which is defined above. The passkey is a unique password shared by the devices when initially paired. Most Bluetooth devices come with a default passkey. The difference between connection and pairing is that the pairing process saves the connection information (device name, passkey, and other information) so that two Bluetooth devices can connect automatically when they are within range of one another. In establishing a wireless connection between a computer and a peripheral, the devices first pair using a pass key, and thereafter can usually connect to choose services. Sometimes subsequent pairing is not necessary after the first time devices are paired and communicate, so pairing will not take place; however, pairing may need to occur if, for example, the stack is somehow reset.

Connection and pairing can be particularly cumbersome in a hospital or other business environment where there may be multiple wireless devices in close proximity. For example, in a hospital, there may be several Bluetooth-enabled devices to monitor a single patient, and one or more patients in a single room. When a user such as a doctor, nurse, or other medical personnel needs to read data from one of the wireless devices, he must perform the following steps: (1) locate all of the wireless devices in the vicinity; (2) pair with a wireless device from which he wants to read data; (3) search the services available in that wireless device; and (4) select and connect to the desired service. Vicinity, as used herein, is defined to include the range in which a wireless device, such as a Bluetooth-enabled device, can connect to the computer. The computer will locate all of the wireless devices that are close enough, or properly situated, to communicate with it. The wireless device may include, for example, medical equipment such as a stethoscope, blood pressure monitor, or glucose monitor. There are other types of wireless devices from which a user may want to read data, including a cellular phone or PDA.

If there are multiple Bluetooth-enabled devices in the vicinity of the user when he attempts to obtain data, the user has to follow the above four steps for each piece of information needed. The needed information may include, for example, the patient's name, identification number, medication types and dosages, blood pressure, pulse, glucose level, etc.

DETAILED DESCRIPTION

Figure 1:
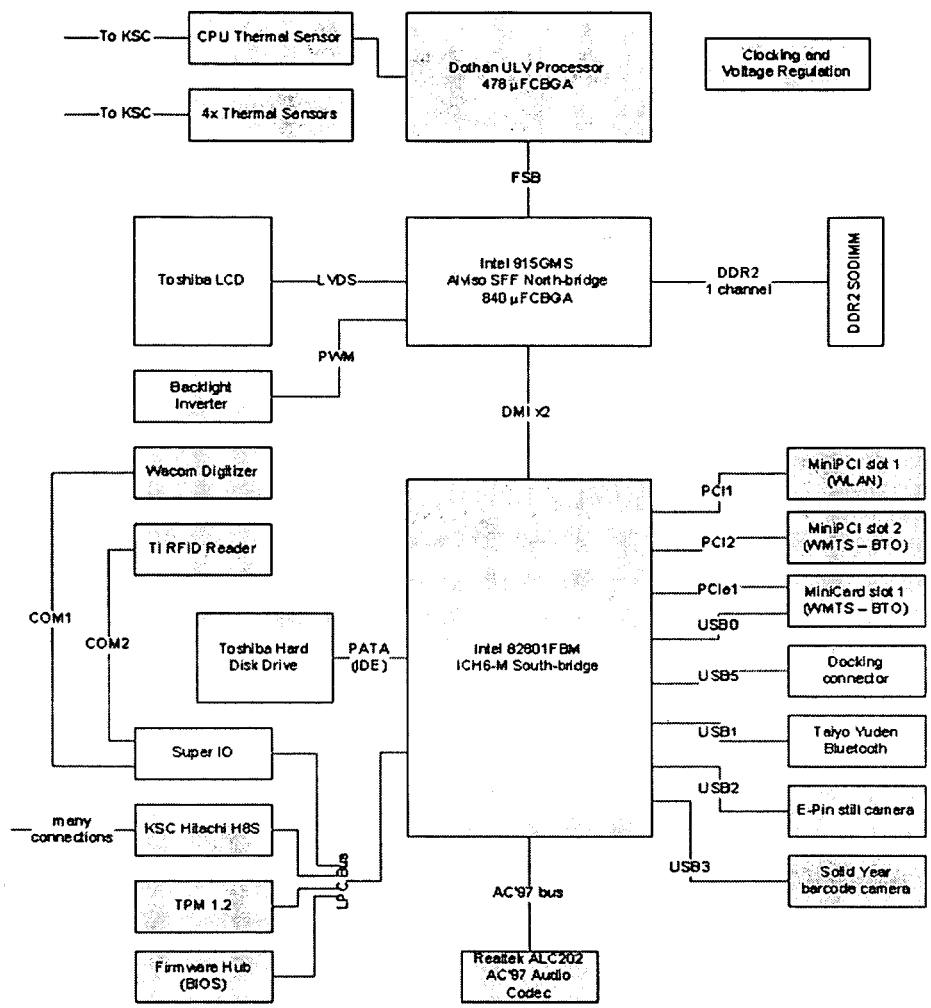
FIG. 1 is a block diagram of an illustrative embodiment of the computing hardware of the present invention.

As used in the specification and claims, the singular forms "a", "an" and "the" include plural references unless the context clearly dictates otherwise. For example, the term "an array" may include a plurality of arrays unless the context clearly dictates otherwise. Further, Table 1, below, lists various acronyms and terms of art used herein.

TABLE 1

| | |
|---|---|
| AC97 | Audio Codec 97 |
| ACPI | Advance Configuration and Power Interface |
| AHCI | Advanced Host Controller Interface (SATA) |
| ALS | Ambient Light Sensor - detects room lighting conditions |
| AOE | Intel MPG APAC ODM Enabling Operation |
| AOL | Alert On LAN |
| AON | Always On. Former name of what is now called EMA. |
| AP | Access Point |
| API | Application Programming Interface |
| ARD | Architectural Requirements Document |
| AV | Audio/Video |
| Azalia | Next generation audio |
| BIA | Back Light Image Adaptation |
| BIOS | Basic Input/Output System, the PC firmware/boot ROM. |
| BLI | Back Light Inverter |
| BT | Bluetooth |
| CCU | Common Configuration Utility |
| CDS | Content Directory Service. A UPnP service that advertises media content available for sharing on a home network. |
| CE | Consumer Electronics (e.g., VCR, stereo, TV) |
| CIR | Consumer Infra Red |
| CLR | Common Language Runtime. Microsoft virtual machine for .NET languages. |
| CMT | Centrino Mobile Technology |
| COM | Common Object Model (software context) or Serial Communications Port (hardware context) |
| CPU | Central Processing Unit |
| CRT | Cathode Ray Tube |
| DDR | Double Data Rate |
| DH | Digital Home |
| DHWG | Digital Home Working Group |
| DLL | Windows Dynamic Link Library |
| DMA | Digital Media Adaptor (Digital Home context) or Direct Memory Access (device driver context). |
| DMI | Direct Media Interface |
| DPG | Intel Desktop Products Group |
| DPST | Display Power Saving Technique |
| DSP | Digital Signal Processor (a chip) or Digital Signal Processing (as in algorithms) |
| DTCP | Digital Transmission Copy Protection |
| DTLA | Digital Transmission Licensing Authority |
| DVB | Digital Video Broadcast. A digital television transmission standards family (as opposed to analog television standards such as NTSC and PAL), used in most regions of the world other than the United States and Japan. DVB-T refers to "terrestrial" (over the air) transmission, DVB-C is cable transmission, DVB-S is satellite transmission, and DVB-H is a format tailored to handheld devices such as cell phones. |
| DVD | Digital Video Disk |
| DVI | Digital Video Interface, a successor to VGA for digital video interface to monitors and TVs. In addition to having digital video pins, the DVI connector also has provision for legacy analog VGA pins, such that a "converter dongle" may be used to adapt a DVI connector to a VGA monitor/projector. Unlike HDMI, DVI connectors can output video only. |
| EBL | Extended Battery Life |
| EC | Embedded Controller, e.g., Hitachi H8 |
| EEPROM | Electrically Erasable Programmable Read Only Memory |
| EF | East Fork - initiative to include multiple new features into a branded platform. Functions and requirements defined in this document. |
| EL | Energy Luminescent panel |
| EMA | Extended Mobile Access |
| EPG | Electronic Program Guide (like a TV Guide, obtained and viewed electronically) |
| ETM | Extended Thermal Model (Camarillo run-time software) |
| FIR | Fast Infra Red |
| FW | Firmware |
| FWH | Firm Ware Hub, the flash memory chip that contains the BIOS |
| GMCH | Graphics Memory Controller Hub |
| GPIO | General Purpose Input Output |
| GPRS | General Packet Radio Service, a system devised to enable data TCP/IP data communication over GSM networks. |
| GPS | Global Positioning System, developed by the U.S. military for navigation and surveying. It relies on satellites for precise determination of locations. |
| GSM | Global System for Mobile communications, the most dominant of all second-generation digital mobile telephony standards. |
| GUI | Graphical User Interface |
| HD | High Definition |
| HDA | High Definition Audio ("Azalia") |
| HDD | Hard Disk Drive |

TABLE 1-continued

| | |
|---|---|
| HDMI | High Definition Multimedia Interface, a successor to DVI for high definition monitors and TVs. It is possible to buy adaptor cables from DVI to HDMI. Unlike DVI, HDMI connectors can also output audio. |
| HIBCC | Healthcare Industry Bar Code standard (data format for asset tagging using barcode or RFID). See http://www.hibcc.org |
| HIPAA | Health Insurance Portability and Accountability Act. See http://www.hipaa.org/ |
| HW | Hardware |
| IA | Intel Architecture. IA-32 is 32-bit architecture. IA-32e is 32-bit architecture with 64-bit extensions. IA-64 is 64-bit architecture (Itanium family). |
| ICH | Input Output Controller Hub |
| ICS | Windows Internet Connection Sharing |
| IHV | Independent Hardware Vendor |
| ISV | Independent Software Vendor |
| IDE | Integrated Device Electronics |
| KSC | Keyboard/System Controller, H8 microcontroller used for keyboard scan, battery charging, and miscellaneous system GPIO's. |
| LAN | Local Area Network |
| LED | Light Emitting Diode |
| LH | Longhorn |
| LOM | LAN On Motherboard |
| LPC | Low Pin Count |
| LTO | Long Term Orbit. A type of Assisted GPS data file obtained over the Internet and optionally cached on the notebook hard drive. This data file contains predictive GPS satellite orbit tracks for 48 hours into the future. |
| LVDS | Low Voltage Differential Signaling, a style of LCD panel interface |
| MCH | Memory Controller Hub |
| MCE | Media Center Edition |
| MDC | Mobile Daughter Card |
| MDH | Mobile Digital Home |
| MEF | Mobile East Fork |
| MPA | Intel MPG Mobile Platform Architecture Operation |
| MPEG | Motion Picture Experts Group, standards body creating specifications for video encoding formats such as MPEG2 and MPEG4. |
| MPG | Intel Mobile Platforms Group |
| MS or MSFT | Microsoft |
| N/A | Not Applicable |
| NAT | Network Address Translation |
| N/C | Not connected. Refers to an optional feature (usually an electrical signal) which is not used on a design, and so is left unconnected. |
| NIC | Network Interface Controller |
| NMA | Network Management Application |
| NMPR | Intel Network Media Product Requirements |
| NOA | Node Observation Architecture |
| NTSC | NTSC is the analog television system in use in Korea, Japan, United States, Canada and certain other places, mostly in the Americas. It is named for the National Television System(s) Committee, the industry-wide standardization body that created it. The term "NTSC" is often used informally to refer to a 525-line/60 Hz (principally USA/Japan) television system, and to differentiate from a 625-line/50 Hz (principally European) "PAL" system. |
| ODD | Optical Disc Drive |
| ODM | Original Design Manufacturer |
| OEM | Original Equipment Manufacturer |
| OOBE | Out Of Box Experience, what the user experiences when they first unpack the product from the box and try to install/use it. |
| OS | Operating System |
| PAL | PAL, short for phase-alternating line, phase alternation by line or for phase alternation line, is a color encoding system used in broadcast television systems in large parts of the world. Other common analog television systems are SECAM and NTSC. PAL was developed by Walter Bruch at Telefunken in Germany, and the format was first introduced in 1967. The term "PAL" is often used informally to refer to a 625-line/50 Hz (principally European) television system, and to differentiate from a 525-line/60 Hz (principally USA/Japan) "NTSC" system. |
| PATA | Parallel AT Attachment, a style of HDD or ODD interface |
| PC | Personal Computer |
| PCB | Printed Circuit Board |
| PCI | Peripheral Connect Interface |
| PDO | Intel MPG Platform Delivery Operation |
| PGA | Pin Grid Array |
| PL | Precision Location |
| PRD | Product Requirement Document |
| PSB | Processor System Bus |
| PVR | Personal Video Recorder, also known as a DVR, Digital Video Recorder |
| PWM | Pulse Width Modulation |
| RAID | Redundant Array of Inexpensive Disks |
| RAM | Random Access Memory |

TABLE 1-continued

| | |
|---|---|
| RFC | "Request For Comment", an IETF specification |
| RFID | Radio Frequency IDentification |
| RIO | UPnP Remote I/O |
| ROM | Read Only Memory |
| RSIO | Reduced Super Input Output |
| RTC | Real Time Clock |
| RX | Receive |
| SATA | Serial AT Attachment, a style of HDD or ODD interface |
| SDVO | Serial Digital Video Output |
| SIO | Super Input Output |
| SIM | Subscriber Identity Module, a miniature "smart card" inserted into GSM phones that may securely contain identification information and encryption keys, as well as in some cases, a protected encryption execution environment. |
| SMC | System Management Controller |
| SMPTE | Society of Motion Picture and Television Engineers (SMPTE) refers to this test pattern as Engineering Guideline EG 1-1990. The components of this pattern are a known standard, so comparing this pattern as received to that known standard gives video engineers an indication how an NTSC video signal has been altered by recording or transmission, and thus what compensation needs to be applied to that signal to bring it back to original condition. The pattern is also used for setting a television monitor or receiver to reproduce NTSC chrominance and luminance information correctly. |
| SOAP | Simple Object Access Protocol, an XML-based lightweight protocol for exchange of information in a decentralized, distributed environment. |
| SODIMM | Small Outline Dual In Line Memory Module |
| Soft AP | Soft Access point |
| SPDIF | Sony/Philips Digital Interface |
| SSL | Secure Sockets Layer |
| STA | Wireless LAN station (client of an AP) |
| STAT | System Thermal Analysis Tool |
| STB | Set Top Box |
| SV | System Validation |
| SW | Software |
| TBD | To Be Determined |
| TPM | Trusted Platform Module |
| TPV | Third Party Vendor |
| TV | Television |
| TX | Transmit |
| UHCI | Universal Host Controller Interface |
| UI | User Interface. Often graphical, see GUI. |
| UPnP | Universal Plug and Play |
| USB | Universal Serial Bus |
| UWB | Ultra Wide Band, former name of Wireless USB |
| VCOM | Virtual COMmunications port, a device driver that looks like a real COM port, but has no physical COM hardware associated with it. |
| VCR | Video Cassette Recorder |
| VGA | Video Graphics Array |
| VO | Visual Off (Energy Lake Lite) |
| VOIP | Voice Over Internet Protocol |
| VPN | Virtual Private Network |
| WLAN | Wireless Local Area Network |
| WMA | Microsoft Windows Media Audio |
| WMTS | Wireless Medical Telemetry Service |
| WMV | Microsoft Windows Media Video |
| WNG | Intel Wireless Networking Group |
| WOL | Wake on LAN |
| WoW | Wake on Wireless LAN |
| WoWLAN | Wake on Wireless LAN |
| WWAN | Wireless Wide Area Network |
| WZC | Windows Zero Configuration, an automatic WLAN configuration scheme. |
| WZP | Windows Zero Provisioning, a follow-on to WZC that also provides for automatic provisioning of DSL at home or WLAN at hotspots. |

To avoid the cumbersome connection and pairing process described above, the present invention contemplates providing an information storage device, such as a radio frequency identification (RFID) tag, that can be used to store the connection and pairing information for any and all wireless devices (e.g., peripherals) to which a computer may need to connect when it is in a particular location. The storage device is spatially separate from the peripheral(s) for which it holds connection and pairing information, as described below. An RFID tag is an object that can be attached to or incorporated into a product, animal, or person for the purpose of identification using radio waves. Chip-based RFID tags contain silicon chips and antennas. The present invention contemplates using other information storage mechanisms besides RFID tags for storing and remotely retrieving data, such as transponders. The information storage mechanism can be used in hospitals, offices, homes, etc., and can be implemented via hardware or software.

In one embodiment, the invention is a method for wireless communication between a first device and a peripheral device, comprising providing a storage device adapted to store communication information for the peripheral device and being readable by the first device, the storage device being spatially separated from the peripheral device. The method also comprises positioning the device so that the first device can read communication information for the peripheral device before communicating with the peripheral device.

The invention also includes an apparatus comprising a storage device including data for wireless communication between a first device and a peripheral device within a location, the apparatus being positioned in or near the location and adapted for storing communication information for the peripheral device. The communication information can be read by the first device, allowing the first device to communicate with the peripheral device.

The invention also includes a method for location-based wireless communication between a first device and a peripheral device, comprising moving the first device to a location within range of a peripheral device, retrieving communication information for the peripheral device from a device other than the peripheral device, and using the communication information to communicate with the peripheral device so that information can be retrieved from the peripheral device.

The invention further includes a method for location-based wireless communication between a first device and a peripheral device. The method comprises obtaining communication information for a peripheral device, storing the communication information on a storage device, moving the first device to a location within range of the peripheral device and the storage device, retrieving communication information for the peripheral device from the storage device, and using the communication information to communicate with the peripheral device so that information can be retrieved wirelessly from the peripheral device. The peripheral device and the storage device are spatially separated.

An illustrative embodiment of the computer (e.g., a tablet PC) for use with the device and method of the present invention is described in detail hereafter and shown in FIG. 1. As shown, the motherboard includes a CPU. In this embodiment, the illustrative CPU is a 478-ball Dothan ULV processor in a Micro-FCBGA package. The CPU may be soldered down to the motherboard or it may be socketed to facilitate the replacement of defective units, to permit the end-user to upgrade the processor, etc. The selected CPU runs nominally at 1.2 GHz in High Frequency mode and at 600 MHz in Low Frequency mode. Other CPUs may be used, although size, heat dissipation, and power requirements may change in other parts of the system. Those skilled in the art will recognize and be able to adapt hardware aspects that must be accommodated for other processors.

Faster processors, for example, may be larger in size and generate more heat while consuming more power; and smaller processors may require less power and generate less heat that must be removed from the system. The selected CPU can also supports enhanced technologies for voltage and frequency scaling.

The system memory may be determined based on the intended application of the tablet PC through the use of commercially available memory modules. The illustrative embodiment of FIG. 1 may contain a single-channel, 400 MHz DDR2 capable SODIMM socket. A default configuration employing one DRAM module of 1 GB size can accommodate a wide-variety of applications, although larger and smaller DRAM modules are available and can be installed at the time of manufacturing. In applications where the memory is not hard-wired to the motherboard and the tablet PC chassis permits opening by the user, the user or technician may be provided with the ability to change memory modules to replace defective units or increase memory capacity.

A variety of commercially-available system clocks may be employed, as well. The present exemplary embodiment employs the CK-410M Clock Synthesizer.

In communication with the processor via the motherboard's front-side bus might be the GMCH, or "North Bridge" as it is commonly referred to in the art. The GMCH (memory and graphics controller) functions can be provided by an Alviso SFF graphics/memory controller hub model "915GMS," and packaged in an 840-ball, 27 mm×27 mm Micro-FCBGA package and is usually soldered to the motherboard. It may, in some instances, be useful to provide the GMCH in a socketed configuration, if convenient substitution of the unit is desirable.

Video capability may be provided via a TFT, LCD, or other flat-panel display that can be incorporated into the chassis of the device. In the present embodiment, only a single display is required, thus the analog TV-Out and digital SDVO outputs can be disabled on the graphics controller. Only the LVDS interface to an LCD panel, or other, is necessary. Other outputs may be enabled and external ports may be provided, with adequate safeguards taken to avoid increasing the risk of liquid incursion into the chassis, in instances where external video is desirable.

The ICH, also referred to as the "South Bridge", provides I/O capabilities. In one embodiment of the present tablet, these services are provided by the ICH6-M I/O controller hub (ICH). This ICH may provide an x2 DMI interface to the "North Bridge", a PCI Bus which can be routed to one or more MiniPCI card connectors, a PCI Express (PCIe) Bus which may be routed to one or more MiniCard card connectors, a PATA interface for providing a data path to a hard disk drive, and a SATA interface. The SATA interface may or may not be used, depending on the number and types of data storage units required. Other storage device interfaces may be used, as well, if a different ICH is selected for use in the tablet.

The ICH can also provide USB ports. The ICH6-M ICH provides Eight (8) USB ports for devices such as cameras, barcode readers, Bluetooth wireless communications controllers, docking connectors, etc. Other ICHs may provide more or less, depending on the needs of the system and the anticipated number of USB peripherals. As well, the ICH should provide an audio bus, to provide the device with sound capability. The ICH of this illustrative embodiment is; configurable for AC'97 or Azalia High-Definiton Audio.

The ICH can also provide a LPC (Low Pin Count) Bus. The LPC bus may connect to the firmware hub, i.e., the Flash EPROM storing the BIOS code and support the use of a KSC or embedded controller (in this embodiment a Hitachi H-8 Keyboard/System Controller). The LPC may also provide a communications path to a Super-I/O chip with two RS-232C serial ports; and a TPM (Trusted Platform Module) chip that provides security key storage. Variations between available ICHs may permit different hardware to be connected to the system via the southbridge to accommodate varying hardware configurations.

The system may also employ thermal sensors to permit monitoring of thermal conditions within the chassis and for various components on the motherboard. Most modern CPU's, such as the one employed in the exemplary embodiment, include an on-die thermal sensor. Further, an external thermal diode positioned very near the CPU package can be connected to a remote thermal sensor. The remote thermal sensor's SMBus may interface with the KSC's SMBus and also with the processor's "Critical Thermal" pin. When the "Critical Thermal" pin is driven, the processor is designed to perform an emergency shutdown. Typically, when such a shutdown occurs, the operating system state will not be saved. Prior to that event, the current temperature can be read via the KSC, and the KSC may also be programmed to provide a warning interrupt when a temperature threshold (also called a "thermal trip point") is crossed. Additional sensors may be employed to increase the level of monitoring or for system-design debugging purposes.

System power may be provided by an internal system battery pack or by mounting in a dock which provides an external connection to an AC/DC converter "brick". The battery pack can be charged through an on-board charger using, for example, a battery charger controller controlled by the KSC. The charger may then be used to charge and control the batteries and provide system regulation of +12.6VDC when external power is provided. When only battery power is available the voltage may typically range from a maximum of about +12.6VDC (fully charged) down to a minimum of about +9.0VDC (at discharge cut-off). Different power supply schemes, of course, may result in variations of the minimum and maximum voltages.

The power from the two paths described above is typically input to most of the on-board voltage regulator circuits to provide power to all system components. The input voltage may be converted by various commercially available components to provide a variety of rail voltages. In the present embodiment, a 4-in-1 controller (e.g., a TPS5130) may be employed to develop the system voltage rails including, at least, +5.0V, +3.3V, +2.5V, and "+1.5V ALWAYS". Other voltage rails may be developed and supplied to peripherals and system hardware by employing appropriate voltage controllers.

Typically, chipset and memory subsystems require separate regulation to provide +1.8V, +0.9V, and +1.05V.

Various "always" power rails may be switched using FETs (Field Effect Transistors) to provide switched rails when system S-states require power to be controlled on or off at various times.

According to the present, illustrative embodiment, six (6) Lithium prismatic cells, such as the Panasonic CGA103450A, are bundled into a single battery pack in a 3S2P geometry. A charging controller board may also be included in this package. Each cell typically provides 1950 mAh of storage nominally at 3.7VDC, for a total pack capacity of 3900 mAh at 11.1VDC.

At an average and continuous system consumption rate, for example about 12 W, a battery life of approximately 3½ hours on a single charge may be anticipated. When the system is in suspend or hibernate mode, battery life will be extended. During times of heavy use (complex computation), battery life will shorten.

The dock may also contain a charging cavity for a second battery, which can preferably be "warm swapped" (exchanged without powering down the system) with a discharged battery while the tablet PC is stationed in the dock and receiving A/C power.

An A/C power "brick" typically provides electrical service to the dock. The A/C power brick may be one such as the Powertron Electronics Corporation model F10653-A. This pack is designed to connect to the wall source power on one end, and the docking cradle on the other end. Such a brick may accept input at 110 VAC to 240 VAC from 47 Hz to 63 Hz, so should be usable worldwide, assuming the correct physical adaptor plug is used. Typically, units manufactured for the North American market might be supplied with a 3-prong (grounded) plug. Other plugs, of course, can be used to accommodate power outlet configurations used elsewhere in the world.

Illustratively, the power brick may provide output at +19 VDC+/−5% at a maximum of about 3.42 A and have a barrel-type plug with positive voltage on "tip" and ground on "ring". Other styles of power bricks to provide for other voltage requirements, lower voltage tolerances, and higher or lower anticipated current requirements are known in the art.

Figure 2:
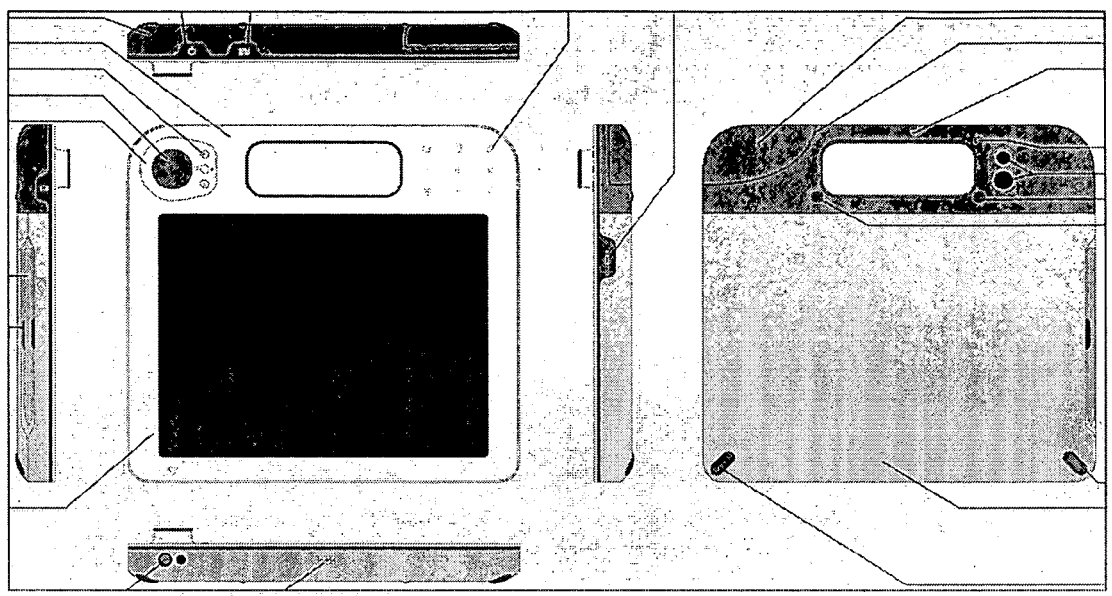
FIG. 2 is a plan view of an illustrative embodiment of the chassis of the present invention.

An embodiment of the tablet PC is illustrated in FIG. 2. As shown, the tablet PC may have a thin and light design targeted to the healthcare vertical market segment and tailored to predicted usage models primarily by nurses and secondarily by doctors. Key system design features might include a rugged, rounded, professional appearance and a sealed chassis resistant to bio-fluids and germ growth. The chassis should be constructed in a manner permitting it to withstand cleaning using anti-bacterial reagents. It is also desirable to provide an ergonomic layout with carry handle and peripheral positioning.

When used to provide a table-style PC for use in hospitals or a clinical environment, the chassis may be designed to provide for the integration of technological features such as a stethoscope, vital signs monitoring equipment (temperature, blood pressure, etc.), or other peripherals desired for medical professionals. In one embodiment, these devices communicate wirelessly with the tablet PC via Bluetooth, 802.11 wireless protocol, or other wireless data transmission protocol.

Figure 3:
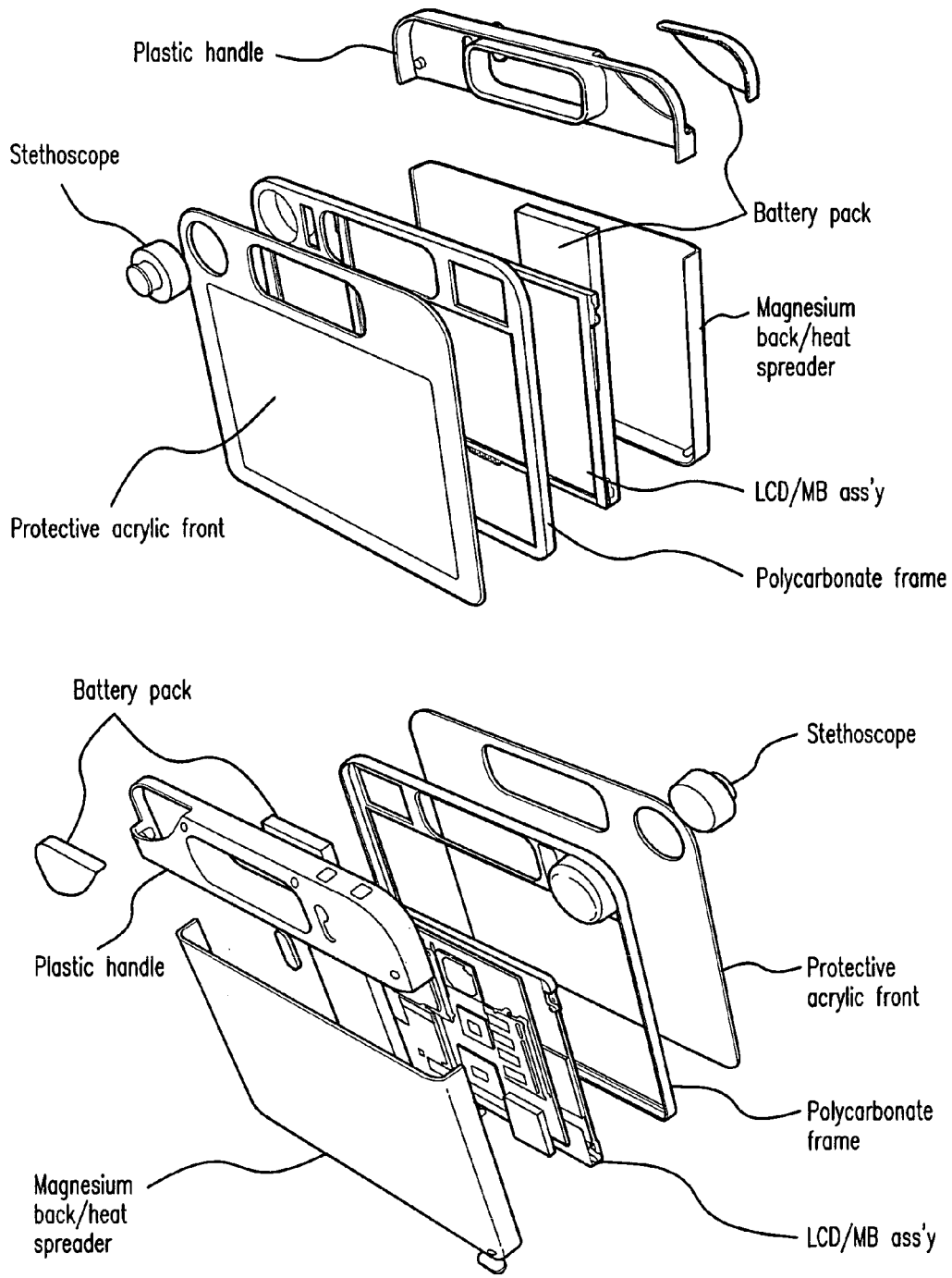
FIG. 3 is an exploded view of an embodiment of the chassis of the present invention.
Figure 4:
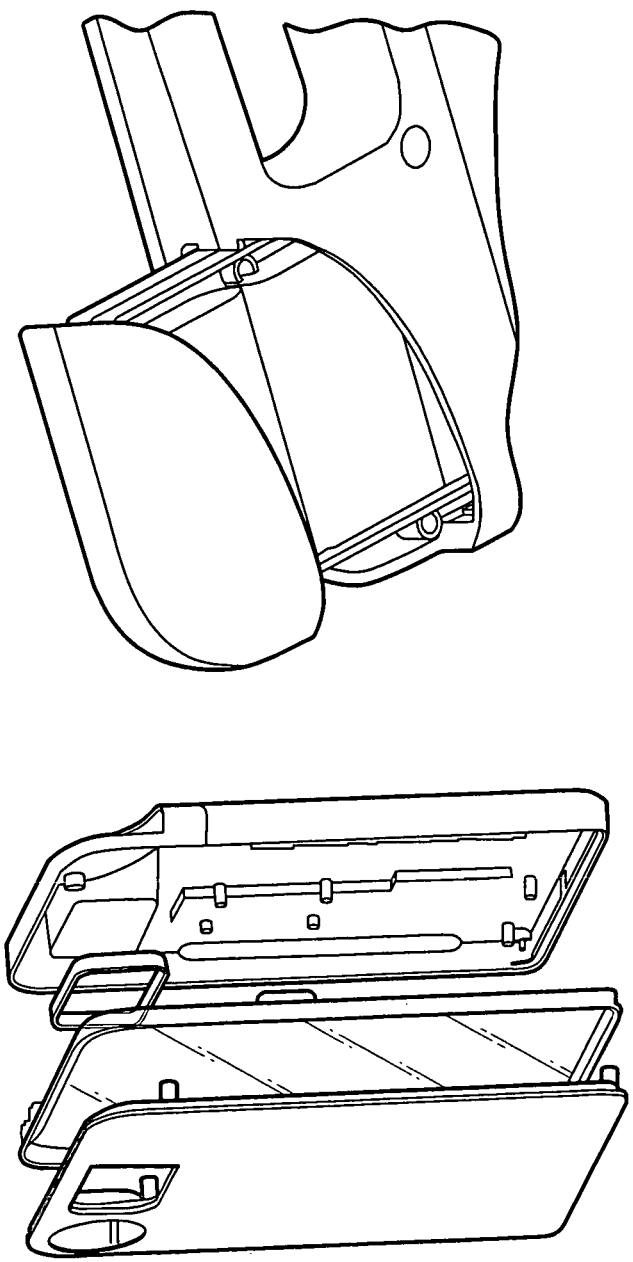
FIG. 4 is an exploded view of an embodiment of the chassis of the present invention showing an exemplary gasket structure.

The chassis may comprise the following components, illustrated in FIGS. 3 and 4: a front plate; frame, an electronic assembly for the LCD or other display screen, a digitizer (not shown), a motherboard (labeled as an MB assembly) and daughter-cards (not shown). A back plate may include a handle assembly and a heat spreader/sink. It may be desirable to provide a back plate that includes a flat-plate comprised of a metal that dissipates heat quickly, such as magnesium, titanium, aluminum, copper, etc. The heat spreader plate may, as well, be in physical contact with motherboard components that require heat dissipation, such as the CPU, although such contact may be made via substances such as thermal grease or intermediate layers of heat-conductive metal. This permits the back-plate of the tablet PC to act as a heat-sink, thereby avoiding the need for internal fans or other means for heat removal that may compromise the unit's ability to resist penetration by fluids, moisture, and other contaminants.

In the illustrative embodiment, the battery pack may incorporate a cap that provides a mating seal to the handle assembly. A stethoscope, or other peripheral, may be formed to insert into a void (or recessed cavity) in the acrylic surface and rest in a cavity sculpted or otherwise formed in the frame. The construction materials, of course, are merely presented for purposes of illustration, those skilled in the art will recognize that a wide variety of metals and plastics may be substituted for any of the chassis components, provided that issues with magnetic and electrical shielding for the components and various antennae are accounted for.

To provide a chassis that is well-sealed to be water/fluid resistant and resistant to cleaning with industrial chemical solvents, or other materials, the chassis components may be assembled with interposing rubber o-ring gaskets, or similar gaskets able to provide fluid-resistance for each of the seams where chassis components meet.

All seams in a system designed to be fluid resistant should generally be gasketed to prevent liquid penetration into the system. A main gasket that seals the top and bottom subassemblies would typically be provided. This gasket also integrates the "hard" buttons (e.g., power, camera shutter, barcode/RFID scanner, etc.) to provide sealed button actuation, where buttons or a button pad are employed.

In an embodiment of the invention, the battery cap contains a rubber diaphragm that forms a compression seal against the handle area. The fasteners preferably use O-rings or silicon for sealed assembly.

In order to achieve a high degree of thermal performance, the primary components may be cooled by the integrated chassis/heatsink. For example, the chassis may be made of injection molded magnesium frame, or other suitable highly heat conductive material. The frame may then be coupled directly to the CPU, MCH, and ICH or indirectly via thermal grease or intermediate layers of heat conductive material.

A thermal shield may be implemented over the top of the chassis/heatsink to limit the heat transfer rate from the heatsink to the user. In a preferred embodiment of the invention, no fans or system vents are provided, which maintains sealability of the system.

According to the structure describe above, the system is passively cooled. Heat is transferred out of the system via conduction, natural convection, and radiation. An insulating shield may be applied to the back of the display screen, for example an LCD, to maintain its required ambient temperature and provide a more uniform temperature profile across the surface of the display.

Figure 5:
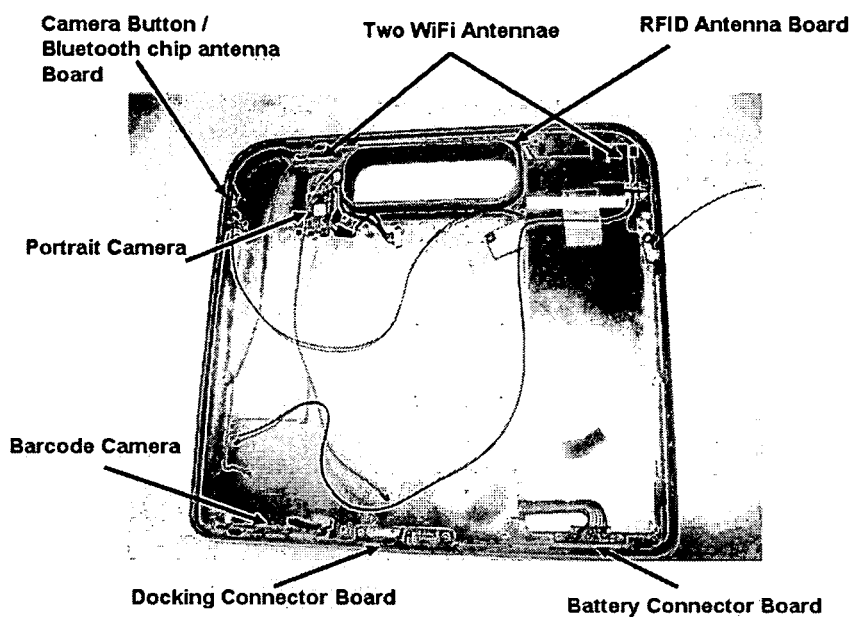
FIG. 5 in a depiction of the inside of the chassis illustrating exemplary placements for antennae according to the present invention.

FIG. 5 illustrates an exemplary placement of a camera button, blue tooth chip antenna board, Wi-Fi antenna, RFID antenna board, battery connector board, docking connector board, barcode camera, and portrait camera in a chassis. Design criteria for component placement may include factors such as magnetic and electrical shielding, thermal shielding or dissipation, RF interference, space constraints, and ergonomics. This list, however, is merely illustrative and not exhaustive of the considerations necessary for component placement; and no single solution may necessarily better than others.

As previously mentioned, the device will ordinarily include a display, such as an LCD, TFT, or other light-weight, portable display. The illustrative system uses an AND Displays 10.4" inch color TFT/LCD Module, model ANDpSi104EA5S-HB. This display supports XGA (1024 (H)×768(V)) screen resolution and 262K (RGB 6-bits data driver) or 16.7M (RGB 8-bits data driver) color depths. The input signals are LVDS interface compatible and it uses a single side-firing CCFL backlight.

Power consumption is 3.7 W typical (using standard SMPTE test pattern) when running at full intensity of 180 nits (cd/m2). Power consumption at 60 nits is 2.87 W. The LCD display, a digitizer, and motherboard may be mated as a single assembly, and shock-mounted to the chassis. The system may also include a backlight inverter (see FIG. 1).

An embodiment of the system includes a DB-15 connector for VGA external display connection, but will ordinarily be unused, as VGA connectors are not sealable. The connector is typically not stuffed on motherboards that are assembled into a chassis, but users requiring external video may desire a tablet PC that offers this feature.

The system may also incorporate a digitizer (see FIG. 1). In the illustrative embodiment, the digitizer is a Wacom SU-001-A 10.4" diagonal electromagnetic (inductive) digitizer that underlaps the LCD. This digitizer has a true resolution accuracy of 0.001 mm (2540 dots/inch) and may report up to 133 points/second during stylus motion.

Figure 6:
FIG. 6 illustrates an embodiment of the present invention incorporating a stylus and recessed caddy within the chassis of a tablet-style PC.

The system may also be equipped with a stylus, to permit data entry directly into the device via the digitizer. In the illustrative embodiment, the stylus is passive. A suitable stylus device includes the Wacom "Penabled Tablet PC Slim Pen", model MP200-00 that is 5.5 mm in diameter. The pen can report 256 different levels of pressure when the stylus is pressed against the acrylic LCD protector. The stylus can be sensed at distances between 5 mm and 14 mm away from the digitizer board (this includes the thickness of the LCD panel, air gap, and a protective acrylic cover). The system may accommodate the stylus in a recessed caddy area, as shown in FIG. 6.

Tablet PC also refers to a computer, such as a personal computer or a mobile computer, incorporating various convenient and intuitive aspects of pencil and paper into a user's interaction with the computer. The term "computer" may include at least one central processing unit or CPU (processor) connected to a host bus. The CPU may be any of various types, including an x86 processor, e.g., a Pentium class, a PowerPC processor, a CPU from the SPARC family of RISC processors, as well as others. The computer system may also include various memory mediums, typically including RAM and referred to as main memory. The main memory may store one or more programs implementing the present invention. The main memory may also store operating system software, as well as other software for operation of the computer system. The term "mobile computer," as used herein, means any computer intended to move location while maintaining functionality. Mobile computers can include, for example, laptop computers, sub-notebooks, personal digital assistants, portable data terminals, tablet PCs, and even smartphones.

To facilitate data and software storage, the system may contain at least one mass storage device, such as an integrated hard disk drive (HDD). Illustratively, the HDD may be a Toshiba 20 Gigabyte 1.8-inch diameter drive, model MK2008GAL. This HDD uses PATA as the interface to the baseboard. There is typically provided a PATA connector directly on the on the baseboard that may be used for a ribbon-cable connection to the "CE" style connector on the HDD. This drive is 5.0 mm thick, making it suitable for use in a portable device such as a tablet PC.

The illustrative embodiment of the tablet PC may include a wireless LAN subsystem. This may consist of a MiniPCI connector on the motherboard, with a Wi-Fi card installed. The commercially available Intel PRO/Wireless 2915 ABG is suitable for use in the illustrative embodiment. It supports the IEEE industry standards 802.11a, b and g.

Certain peripheral devices may be connected to the tablet PC via wireless LAN or Bluetooth technology. The present device may, therefore, also incorporate a Bluetooth controller such as the Taiyo Yuden EYSFCCSXX module, to provide Bluetooth capability for the system. This device incorporates the CSR (Cambridge Silicon Radio) "Bluecore 4" radio chip, operating in the 2.4 GHz band. The module implements Bluetooth 2.0 specifications, and includes AFH (advanced frequency hopping) and EDR (enhanced data rate) functions. The module interfaces to the system using one of the USB ports available via the ICH.

The Taiyo Yuden EYSFCCSXX module also supports WiFi coexistence "Phase 2" capability. This reduces the interference between the Bluetooth and the WiFi radios when they are operating simultaneously. The two modules have a communication channel that they use to inform one another about when they are transmitting, and what WiFi channel is being used. The Bluetooth module attempts to choose a different channel in the 2.4 GHz band which does not conflict with the WiFi channel in use (determined by access point association).

The WMTS subsystem may also include a "dual stuffing option" connector layout on the motherboard. The motherboard, therefore, may contain contacts ("pads") for both MiniPCI and MiniCard (aka Mini-PCI Express) socket connectors. These pads are designed to use substantially the same physical volume inside the system.

An OEM employing this feature would determine, at manufacturing time, which connector to solder to the motherboard, since most compact chassis layouts will permit only one can be used at a time. Then the OEM may insert the appropriate form-factor WMTS card into the system before sealing the chassis.

In instances where the tablet PC user will benefit from having an RIFD reader incorporated into the device, a suitable hardware solution may include the Texas Instruments 7961 RFID reader chip and companion MSP430 microcontroller. This device may be connected via an RS-232 interface at TTL levels (i.e., +5VDC and Ground, vs. the more conventional +12VDC and −12VDC) to the COM2 port of the Super-IO. This T.I. chip supports RFID protocols ISO 15693, ISO 14443, and T.I.'s "Tag-It".

The RFID reader is a relatively low power device and has a short reading range on the order of 4 to 5 centimeters. Its antenna should be positioned as far away from any metal as reasonably possible, to read effectively. As a result, the user should position the RFID-tagged object near the antenna location for scanning.

An audio subsystem may be incorporated into the device to provide sound output. One suitable device is based on a Realtek ALC202 codec, which is compliant with the AC'97 specifications. The system may also contain an internal power amplifier to more effectively drive the internal speaker. Exemplary of such amplifiers is the LM4960SQ. A single mono speaker, a custom-designed piezo-electric transducer, can provide rudimentary audio output. The transducer may be mounted to the back of the display screen protector in the area between the medical peripheral slot (stethoscope) and the handle cutout. If higher-quality audio output is desired, a Bluetooth headset may be used, to avoid the need to add I/O ports to the chassis. For that same reason, the illustrative embodiment employs a microphone input via a Bluetooth headset when sound is desired.

In order to avoid increased risk of penetration by liquids and contaminants, the tablet PC will generally not include externally accessible audio I/O jacks, as such jacks would create difficulties in maintaining the sealed nature of the system. If for any reason the end user requires external audio jacking, a USB audio device (e.g., Creative SoundBlaster Audigy 2 NX) may be installed into one of the free USB ports in the dock.

Figure 7:
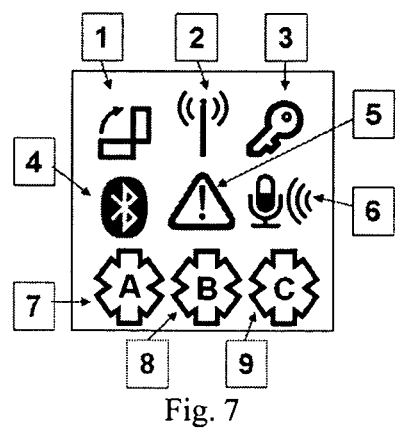
FIG. 7 illustrates an embodiment of a touchpad module.
Figure 8:
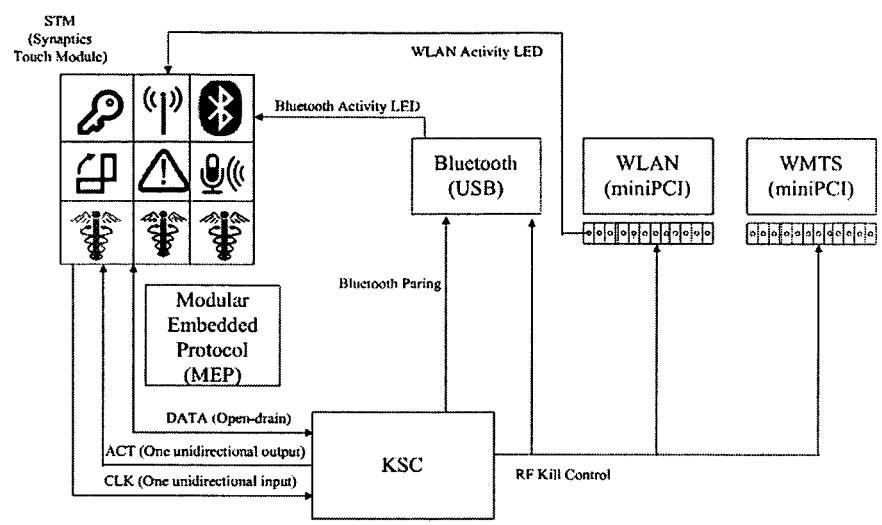
FIG. 8 illustrates a touchpad module and block flow diagram of a possible architecture for use of a touchpad in connection with the hardware of the present invention.
Figure 9:
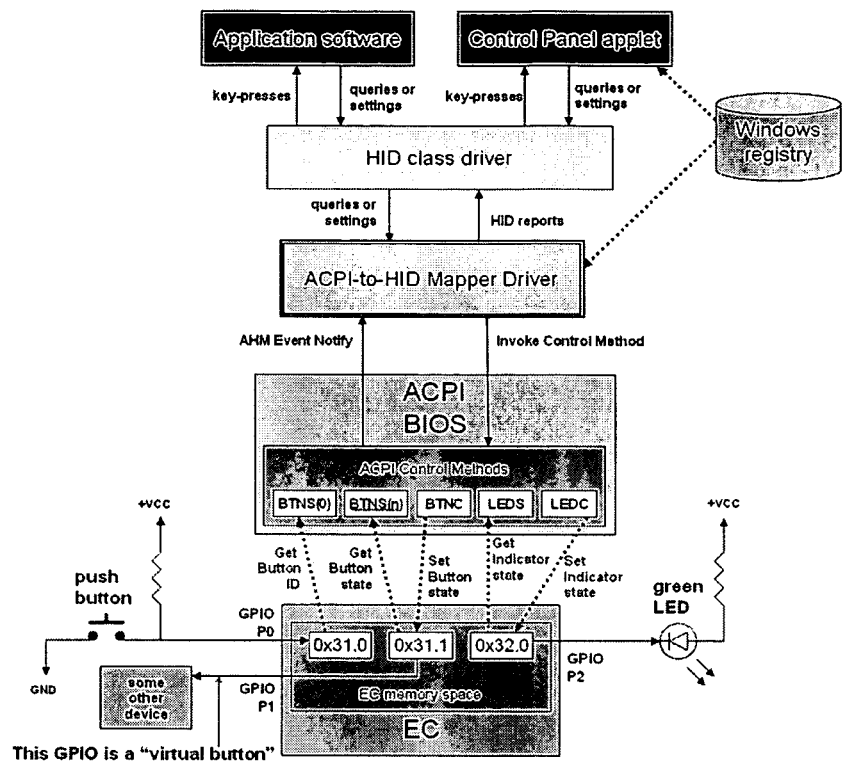
FIG. 9 illustrates an embodiment of an APCI-to-HID Mapper driver architecture.

The system integrates a number of buttons and indicators, the functions and features of which are illustrated in FIGS. 7-9. Each button is assigned a "button number" which refers to the button ID assigned by the KSC. This number may be used by the KSC to report button presses to an ACPI-to-HID mapper driver. This driver may then translates the button press into an HID code for further processing. The system may include "soft" buttons. A "soft" button is one managed by the Synaptics Touch Module (STM); there is no tactile feedback from these capacitive buttons. A "hard" button is a physical momentary switch that includes tactile feedback. A "virtual" button does not have a user-accessible physical existence; it is only a software-controllable abstraction of a GPIO signal that can be driven by the KSC.

The "STM" refers to the Synaptics Mobile Touch Module, a commercially available product which may be used in accordance with the illustrative embodiment of the invention. Other button-handling solutions will be recognized by those skilled in the art and are contemplated by the present invention. The STM may contain both capacitive buttons and LEDs integrated into a single package. The STM interfaces to the KSC using a "MEP" protocol defined by the manufacturer.

The illustrative device will generally include a power button that is used to turn the system on and off, and also to put a running system into sleep or hibernate modes (per Windows Control Panel configuration settings, when a Windows O/S is used). The KSC monitors the user press of a physical button and sends onward the appropriate signal to the power and voltage regulation circuitry. In addition, the KSC monitors the CPU state as represented by status pins on the ICH, and may reflect the appropriate status condition on a power LED.

The applet may respond to the HID code by instructing the KSC to power-up the camera and RFID readers, turn on the white illumination LED, and then via USB instruct the camera to grab image frames for barcode analysis and decoding. Simultaneously, via an RS-232 interface, the RFID reader may be instructed to begin searching for nearby RFID tags. When either one of the barcode decode or RFID scanning functions returns a successful result, the applet may instruct the KSC to turn off the illumination LED, power-down the camera, and the RFID reader.

Synaptics Touch Module (STM) soft buttons may be used for various system management functions. The STM can contain an embedded microcontroller that interfaces to the KSC using a "MEP" (Modular Embedded Protocol) interface. When the STM reports a button press to the KSC, the KSC sends an SCI interrupt signal to the ACPI framework. This is delivered to the ACPI-to-HID Mapper driver which translates it into the appropriate HID button code. An applet responds to the HID code by performing the appropriate function, and in some cases, instructing the KSC to turn on or off specific LEDs by forwarding the command to the STM. In one embodiment of the invention, wireless activity status LEDs (for either or both WiFi and Bluetooth) are driven to the STM directly by the wireless card(s) rather than via the KSC. A performance advantage may be gained in this manner.

For security, a device such as the Infineon SLB9635TT TPM may be used to store credentials securely on the notebook. This device is packaged in a 28-pin TSSOP package, and connects to the ICH via the Low Pin Count (LPC) bus. It is compliant with TPM 1.2 specifications.

Figure 10:
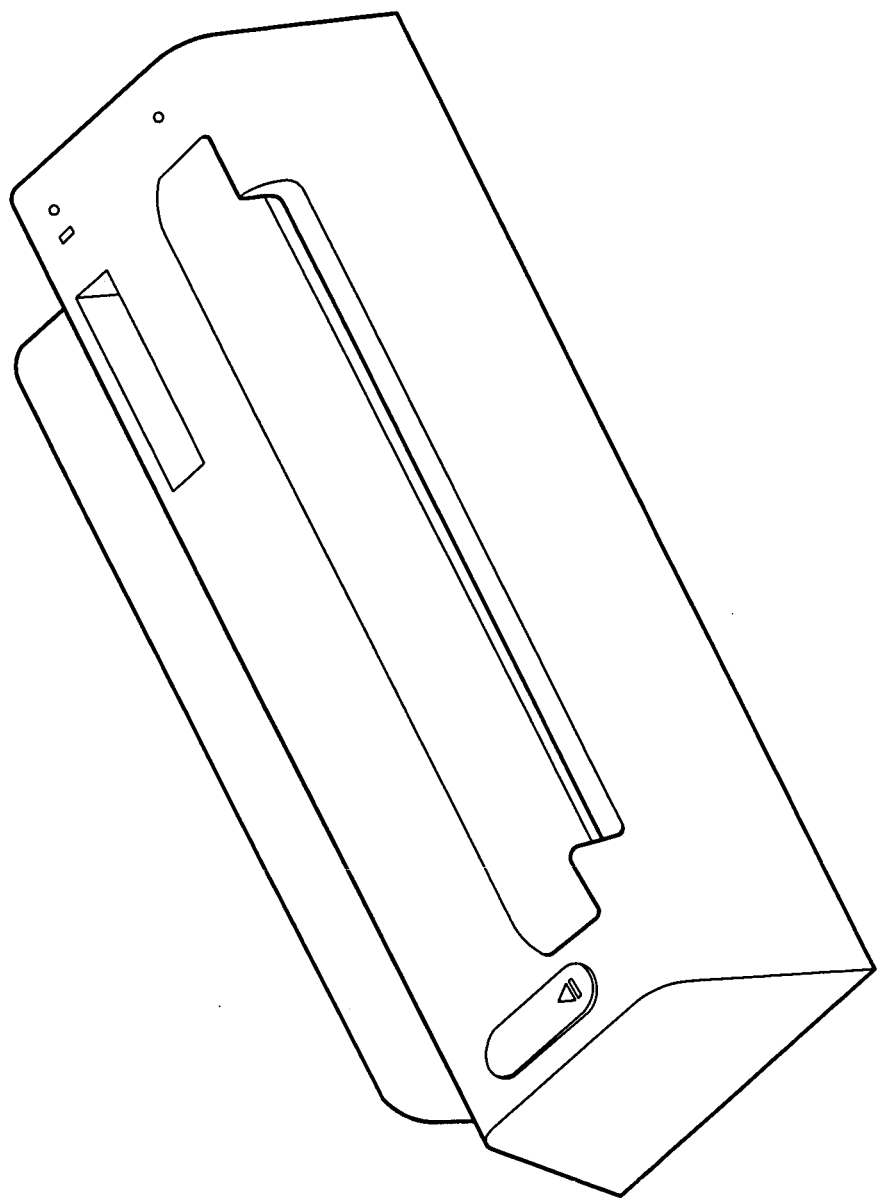
FIG. 10 is a perspective view of an embodiment of a docking station according to the present invention.
Figure 11:
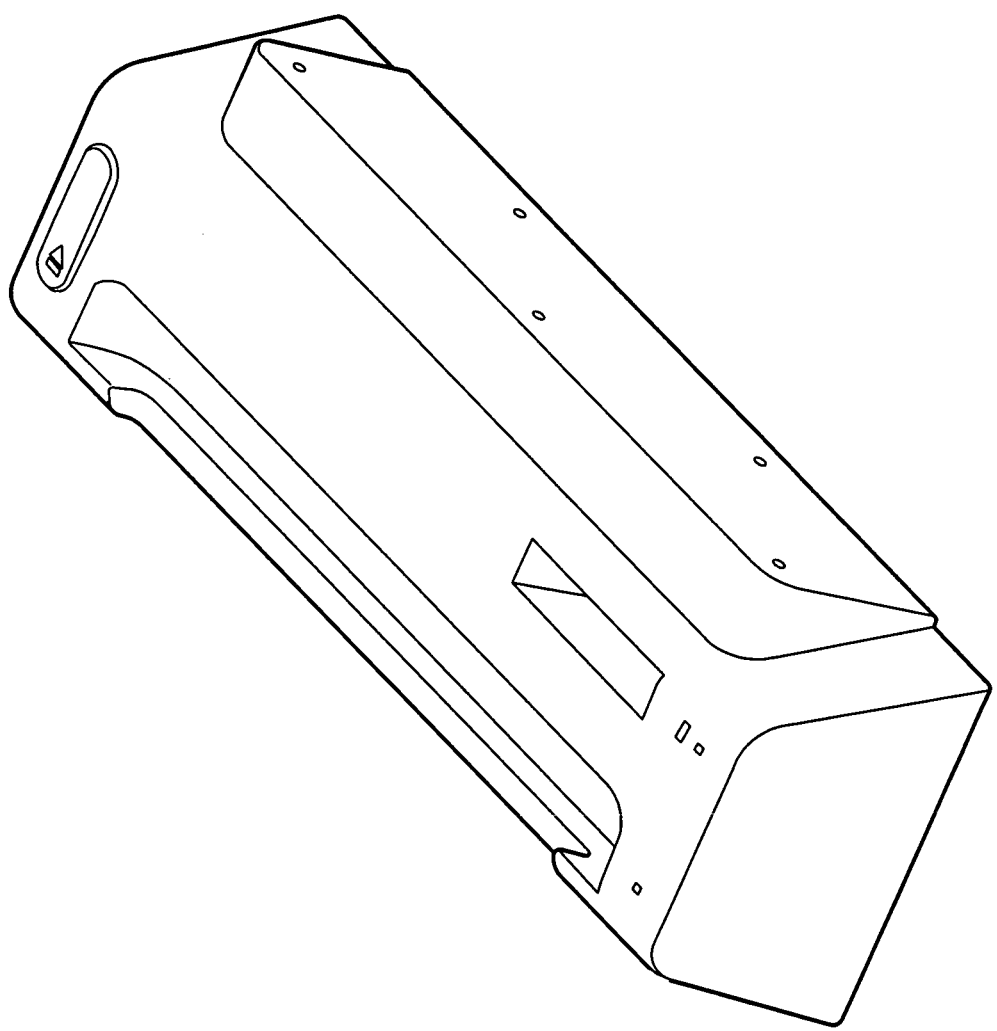
FIG. 11 is another perspective view of an embodiment of a docking station according to the present invention.
Figure 12:
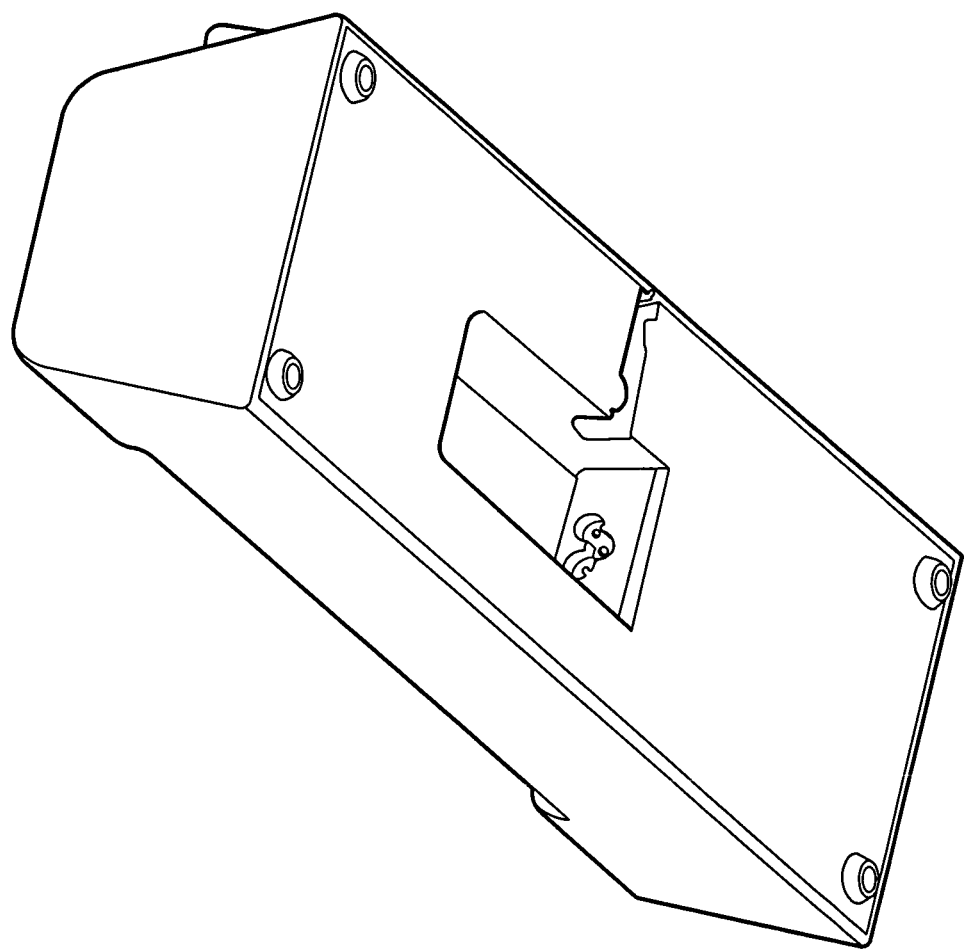
FIG. 12 is a perspective view of an embodiment of a docking station according to the present invention showing the bottom of a docking station.

The tablet PC user will typically desire a "dock" for the tablet PC. The device may be inserted into the dock to recharge the batteries and to add additional functionality to the device via additional I/O ports, external graphics ports, etc. An embodiment of the dock is illustrated in FIGS. 10-12. The dock is preferably configured to house the tablet PC in a manner that allows it to stand upright and still have the screen be completely viewable. It might include battery charging contacts for the tablet, as well as a charging cavity for a spare battery. LED indicators can be provided to communicate charging status.

The dock may contain a USB hub (presently, USB 2.0 is the most common solution). USB functionality may be implemented with a device such as the Philips ISP 1520 USB controller chip in an LQFP64 package. The hub chip has 1 upstream port (goes to the docking connector) and 4 downstream ports. Of the 4 downstream ports, 3 of them are exposed as external USB "type B" sockets. The final downstream port connects to the Ethernet chip. The hub supports USB2.0 data transfer at high-speed (480 Mb/s) and at legacy (USB 1.1) full-speed (12 Mb/s) and low-speed (1.5 Mb/s) rates.

The dock may also contain an Ethernet (IEEE 802.3) interface. This might be implemented with the Asix AX88772LF chip in a LQFP128 package The Ethernet chip, desirably, contains both MAC and PHY in a single package, and supports USB2.0 and 802.3 operation at 100 Mb/s and 10 Mb/s.

The Ethernet interface may be available on the dock via an external RJ45 socket. An docking connector, in the figures shown as a flush-mounted, injection molded port, provides power and USB connectivity between the tablet PC and the dock. The dock will, generally, also include necessary A/C power components and cabling.

Figure 13:
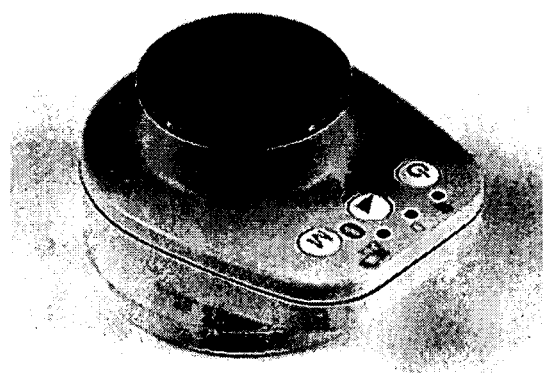
FIG. 13 is a perspective view of an embodiment of a wireless stethoscope.

An illustrative embodiment of the tablet PC includes at least one peripheral data-acquisition device for use by healthcare professionals. Such a device might include a Bluetooth-enabled stethoscope, as shown in FIG. 13, for use by a clinician to examine heart and lung sounds of patients. The stethoscope may include a rechargeable battery (or non-rechargeable battery) and be capable of transmitting audio-output directly to a headset worn by the user (typically the headset will also be Bluetooth-enabled). Alternatively, the stethoscope may transmit to the tablet PC and the tablet PC retransmit the audio output to a headset worn by the user or play the sound via the tablet's internal audio system and speaker.

The stethoscope may include numerous buttons and indicators to permit the user to change the audio output device, set the type of measurement being taken, and perform basic functions (such as turn the device on and off). The stethoscope may also transmit information to the tablet PC relating to battery level, include audio filters to permit more accurate audio representation of a patient's heartbeat, lung function, etc., or include other functions desired by the healthcare professional.

There are instances where a computer such as a tablet PC is moved to multiple locations for information retrieval, and each location has one or more peripherals from which the tablet PC must retrieve information. One scenario is a tablet PC used in a hospital, where there are multiple patient rooms (locations) and multiple peripheral devices (heart rate monitor, blood pressure monitor, stethoscope, blood oxygen level monitor, etc.) in each room. A user, such as a nurse enters must collect information from the peripherals for the patient in each room. In a scenario where the peripherals are wireless, communication (e.g., connection and pairing) with the peripherals associated with each patient can be complex and time consuming. Using an example of Bluetooth enable wireless peripherals and user computer, the user would have to send a general inquiry, review a list of available Bluetooth-enabled device (which could include all devices within wireless range of the user computer, whether hospital-owned or not) and then identify and select the appropriate devices needed to collect information from the patient. Further, the user will need to know security codes for some or all of the devices.

The present invention enables simplification of this process by storing communication information, such as connection and pairing information, on a storage device. Communication information is stored for each wireless peripheral within the location from which a user may want to collect information. For example, in a hospital room having a Bluetooth-enabled heart rate monitor, blood pressure monitor, stethoscope, and blood oxygen level monitor, connection and pairing information for each device is stored to a storage device (e.g., an RFID tag) that is placed in the hospital room. Upon entering the room to collect patient information, the nurse need only initiate software on her computer that reads the storage device (e.g., via an RFID reader) and connects and pairs with all of the devices as available or allows the nurse to easily connect and pair with each device in turn, to collect the needed information.

An embodiment of the invention contemplates a user such as a hospital administrator storing the communication information for appropriate wireless peripheral devices for each location such as a hospital room. For Bluetooth-enabled devices, the administrator could obtain connection information via inquiry or device documentation, and would likely obtain pairing information from device documentation. According to an embodiment of the invention where the storage device is location-specific and preferably housed in or near the location, the stored communication information would only have to be revised if a wireless peripheral was added or changed.

In another embodiment of the invention where the storage device is patient-specific (such as one that is included in a patient's identification bracelet), a user such as a hospital administrator would have to determine the wireless peripherals to be used for that patient (for example, by determining the patient's room) and then store the information on a storage device on a patient-by-patient basis.

As stated above, an embodiment of the present invention uses a storage device such as an RFID tag to store communication information including connection and pairing information for one or more compatible wireless peripherals. Pairing information can include, for each peripheral device, the address of the device, the class of the device, the device name, and a passkey for the device. Connection information can include, for each peripheral device, the address of the device, the class of the device, the device name, service classes of any services that the device supports (e.g., A2DP Service, SerialService), and the names of any services that the device supports. Therefore, in an embodiment of the invention, the information stored in the storage device includes, for each peripheral in a location, the address of the device, the class of the device, the device name, its passkey, service classes of any services that the device supports (e.g., A2DP Service, SerialService), and the names of any services that the device supports.

Peripheral, as used herein, broadly refers to devices that can be added to a host computer in order to expand its capabilities. Peripheral devices are commonly optional in nature. The present invention contemplates peripherals to include any device that can provide information to a computer or enhance its functionality.

The present invention will hereinafter be discussed with respect to Bluetooth-enabled devices. It is to be understood, however, that any suitable wireless communication protocol can be used and is contemplated by the present invention, and may require alternative communication (connection and pairing) information and/or procedures. A Bluetooth device, such as a computer, playing the role of the "master" can presently communicate with multiple devices playing the role of the "slave". At any given time, data can be transferred between the master and 1 slave; but the master can switch rapidly from slave to slave in a round-robin fashion. The present invention contemplates such sequential transmittion from the master to one or more slaves, as well as simultaneous transmission from the master to multiple slaves.

Figure 14:
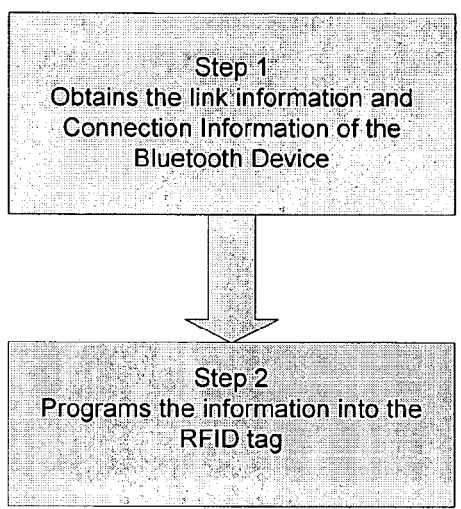
FIG. 14 is a schematic diagram of two processes comprising an embodiment of the invention.
Figure 14:
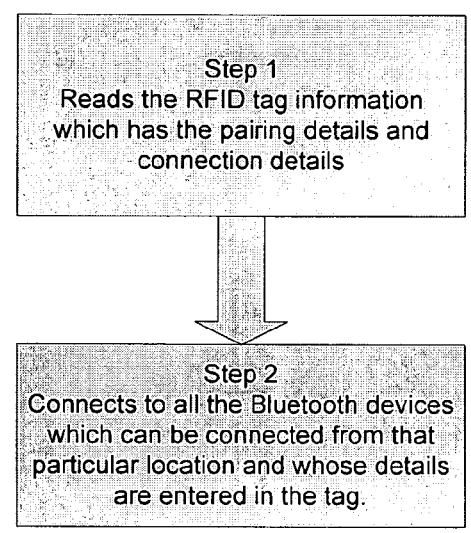

An embodiment of the present invention performs two processes, as illustrated in FIG. 14. The first process, Process 1, obtains and stores communication information for all wireless devices that can be or are intended to be connected to the computer in a particular location. The term "location," as used herein to describe the computer and the peripheral that are communicating wirelessly, broadly refers to any defined area such as a room or broadcast range for a wireless device. The connection and pairing information is read or otherwise obtained in Step 1, and is then stored on a readable medium (or "storage device") in Step 2, such as an RFID tag located in or near the location.

In Process 2 of FIG. 14, a device such as a computer reads the communication information from the storage device for the predetermined wireless devices. The communication information allows the device to communicate with wireless devices. In the embodiment illustrated in FIG. 14, the devices are Bluetooth-enabled and the readable medium is an RFID tag. The communication information necessary for a Bluetooth-enabled device is set forth above. As an alternative to using a storage device such as an RFID tag, the communication information can be broadcast by a device located within the area. After reading the communication information, the computer can be connected automatically or manually (i.e., via user initiation) to the wireless devices whose information was stored on the readable medium.

Once a connection has been made, the computer determines which services are available for that device. In an alternate embodiment of the invention, the storage can be located outside of the area or location of the peripherals, for example at a location so that communication information can be retrieved prior to entering the location.

The term "services," as used herein, refers to the profiles that a particular Bluetooth device can support. Bluetooth profiles are developed to describe how implementations of user models are to be accomplished. The user models describe a number of user scenarios where Bluetooth performs the radio transmission. A profile can be described as a vertical slice through the Bluetooth protocol stack. It defines options in each protocol that are mandatory for the profile. It also defines parameter ranges for each protocol. Profiles are used to decrease the risk of interoperability problems between different manufacturers' products. Exemplary services available in an embodiment of the present invention would include the A2DP Profile and the Serial Port Profile.

The information needed for wireless connection and pairing for a Bluetooth-enabled device can be obtained from each device's Bluetooth stack. A Bluetooth stack is software that allows Bluetooth devices to be recognized and used. A stack can also refer to software that resides on Bluetooth devices and controls Bluetooth communication from the hardware level. Other wireless communication devices may use other stacks or similar software to facilitate connection and pairing.

EXAMPLE

Figure 15:
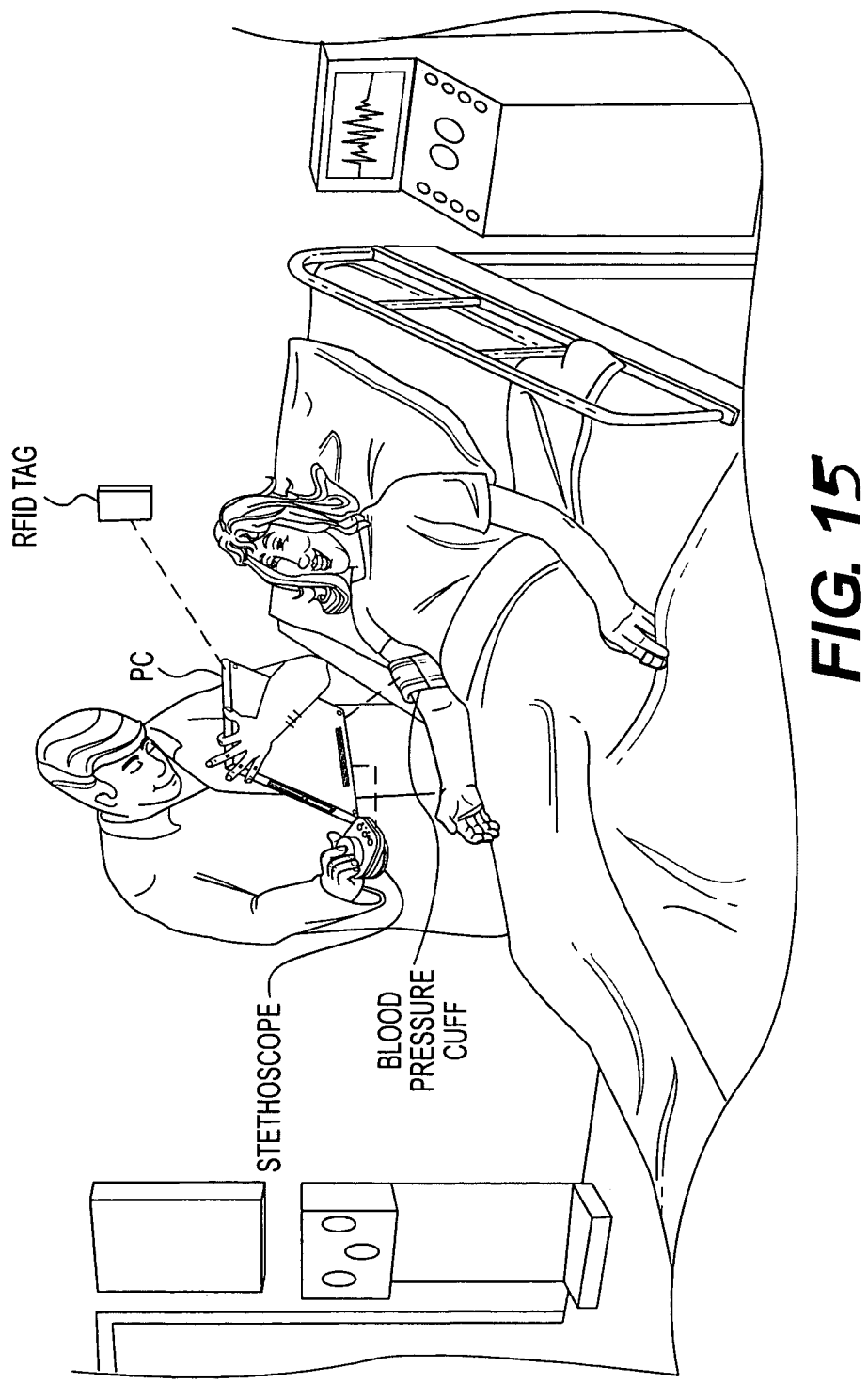
FIG. 15 illustrates an exemplary embodiment of the invention, implemented in a hospital setting.

FIG. 15 illustrates an exemplary use of an embodiment of the present invention. In the exemplary use, a doctor, nurse, or other care giver enters a location such as a patient's room in a hospital, clinic, or other medical facility to gather data regarding the patient. First, the care giver uses his computer to retrieve communication information for predetermined peripherals within the location from an RFID tag situated in the location. Retrieval of communication information may be automatically initiated by the computer or manually initiated by the care giver. The computer uses the communication information to connect to/pair with the peripherals whose information it received. Connection to the peripherals may be automatically initiated by the computer or manually initiated by the care giver. The peripherals include, in this exemplary use, medical peripherals such as a wireless stethoscope, a wireless blood pressure monitor, and a wireless pulse meter. After connection/paring takes place, the computer can communicate with the peripherals to send and receive data regarding the patient.

In an embodiment of the invention where connection and information retrieval is manually initiated by the care giver, after a wireless connection has been established, a list of available wireless devices can be displayed to the care giver, and the care giver may select one or more of the devices from which to retrieve information. For example, if the computer has connected to a Bluetooth-enabled wireless blood pressure monitor, the care giver may select that device and use the computer retrieve information regarding the patient's blood pressure. After retrieving information from the blood pressure monitor, the care giver may select one or more additional wireless devices from which to retrieve information, such as a pulse monitor or a stethoscope.

After the care giver has retrieved the information that he needs, the mobile computer can be disconnected from the wireless devices manually or automatically.

The invention claimed is:

1. A method comprising:
   providing a storage device adapted to store communication information for at least one of more than one peripheral devices and being readable by a first device, wherein the communication information for the at least one of the more than one peripheral devices includes information used to establish communication between the at least one of the more than one peripheral devices and the first device, the storage device being spatially separated from the more than one peripheral devices and the first device; and
   positioning the storage device so that the first device reads the communication information for the at least one of the more than one peripheral devices before communicating with the at least one of the more than one peripheral devices.

2. The method of claim 1, wherein the first device and the more than one peripheral devices are in the same location when communication between the first device and the more than one peripheral devices takes place.

3. The method of claim 2, wherein the storage device is positioned in the location.

4. The method of claim 3, wherein the location is a room.

5. The method of claim 4, wherein the room is in a hospital or medical clinic.

6. The method of claim 1, wherein the communication information includes connection and pairing information.

7. The method of claim 1, wherein the first device can read the storage device.

8. The method of claim 1, wherein the more than one peripheral devices and the first device are Bluetooth-enabled and communication is accomplished using Bluetooth protocols.

9. A method comprising:
   locating a first device to a location within range of more than one peripheral devices;
   retrieving communication information for at least one of the more than one peripheral devices from a storage device that is arranged spatially separate from the first device and the more than one peripheral devices, wherein the communication information includes information used to establish communication between the first device and the at least one of the more than one peripheral devices; and
   using the communication information to establish communication with the at least one of the more than one peripheral devices.

10. The method of claim 9, wherein the first device and the more than one peripheral devices are in the same location when communication between the first device and the more than one peripheral devices takes place.

11. The method of claim 10, wherein the storage device is positioned in the location.

12. The method of claim 11, wherein the location is a room.

13. The method of claim 12, wherein the room is in a hospital or medical clinic.

14. The method of claim 9, wherein the communication information includes connection and pairing information.

15. The method of claim 9, wherein the first device can read the storage device.

16. The method of claim 9, wherein the more than one peripheral devices and the first device are Bluetooth-enabled and communication is accomplished using Bluetooth protocols.

17. An apparatus comprising a storage device configured to store data for wireless communication between a first device and at least one of more than one peripheral devices, the apparatus being spatially separated from the first device and the more than one peripheral devices, and adapted for storing communication information for the at least one of the more than one peripheral devices,
wherein the storage device is configured to provide the communication information to the first device, wherein the communication information is configured to establish communication between the first device and the at least one of the more than one peripheral devices.

18. A method comprising:
obtaining communication information for at least one of more than one peripheral devices, wherein the communication information is stored in a storage device and includes information to establish communication between a first device and the at least one of the more than one peripheral devices;
locating the first device to a location within range of the more than one peripheral devices and the storage device, the more than one peripheral devices, the first device, and the storage device being spatially separated;
retrieving the communication information from the storage device; and
using the communication information to establish communication with the at least one of the more than one peripheral devices.

19. The method of claim 1, wherein the communication information is selected from the group consisting of: an address of each of the peripheral devices, a class of each of the peripheral devices, a name of each of the peripheral devices, a passkey of each of the peripheral devices, service classes of any services that each of the peripheral devices support, and names of any services that each of the peripheral devices support.

20. The method of claim 19, wherein service class is selected from the group consisting of: A2DP Service and SerialService.

21. The method of claim 9, wherein the communication information is selected from the group consisting of: an address of each of the peripheral devices, a class of each of the peripheral devices, a name of each of the peripheral devices, a passkey of each of the peripheral devices, service classes of any services that each of the peripheral devices support, and names of any services that each of the peripheral devices support.

22. The method of claim 21, wherein service class comprises A2DP Service or SerialService.

23. The apparatus of claim 17, wherein the more than one peripheral devices include a data-acquisition device arranged to perform healthcare operations.

24. The apparatus of claim 23, wherein the data-acquisition device is selected from the group consisting of: a Bluetooth-enabled stethoscope, a Bluetooth-enabled heart rate monitor, Bluetooth-enabled blood pressure monitor, and Bluetooth-enabled blood oxygen level monitor.

25. The apparatus of claim 18, wherein the more than one peripheral devices includes a data-acquisition device arranged to perform healthcare operations.

26. The apparatus of claim 25, wherein the data-acquisition device is selected from the group consisting of: a Bluetooth-enabled stethoscope, a Bluetooth-enabled heart rate monitor, Bluetooth-enabled blood pressure monitor, and Bluetooth-enabled blood oxygen level monitor.

27. The method of claim 1, wherein the storage device includes a Radio-Frequency Identification (RFID) tag.

28. The method of claim 9, wherein the storage device includes a RFID tag.

29. The apparatus of claim 17, wherein the storage device includes a RFID tag.

30. The method of claim 18, wherein the storage device includes a RFID tag.

31. The method of claim 27, wherein the first device includes an RFID reader configured to read communication information stored in the RFID tag.

32. The method of claim 28, wherein said retrieving operation is performed using an RFID reader.

33. The apparatus of claim 29, wherein the first device includes an RFID reader configured to read communication information stored in the RFID tag.

34. The method of claim 30, wherein said retrieving operation is performed using an RFID reader.

35. The method of claim 34, wherein the RFID reader is operatively associated with the first device.

36. A method comprising:
using communication information to establish communication between a first device and at least one of more than one peripheral devices, wherein:
the first device is configured to obtain the communication information from a storage device containing the communication information;
the communication information includes information to establish communication between the first device and the at least one of the more than one peripheral devices; and
the first device is located within range of the more than one peripheral devices and the storage device, the more than one peripheral devices, the first device, and the storage device being spatially separated.

* * * * *